United States Patent [19]

Chase et al.

[11] Patent Number: 5,014,288
[45] Date of Patent: May 7, 1991

[54] X-RAY COATING WEIGHT CONTROLLER AND SENSOR

[75] Inventors: Lee M. Chase, Los Gatos; John D. Goss, San Jose, both of Calif.

[73] Assignee: Measurex Corporation, Cupertino, Calif.

[21] Appl. No.: 341,639

[22] Filed: Apr. 20, 1989

[51] Int. Cl.$^5$ .......................................... G01N 23/083
[52] U.S. Cl. ........................................ 378/53; 378/54; 378/55
[58] Field of Search ....................... 378/44, 45, 50, 51, 378/53–56, 157

[56] References Cited

U.S. PATENT DOCUMENTS

| Re. 30,884 | 3/1982 | Buchnen | 378/53 |
|---|---|---|---|
| 3,435,220 | 3/1969 | Hanken | 378/53 |
| 3,452,193 | 6/1969 | Petersen | 378/157 |
| 3,904,876 | 9/1975 | Arendt | 378/53 |
| 3,974,386 | 8/1976 | Mistretta et al. | 378/157 |
| 4,090,074 | 5/1978 | Watt et al. | 378/53 |
| 4,668,867 | 5/1987 | Lingenfelter | 378/53 |
| 4,815,116 | 3/1989 | Cho | 378/53 |
| 4,845,730 | 7/1989 | Mercer | 378/51 |

FOREIGN PATENT DOCUMENTS 2044443 10/1980 United Kingdom .

OTHER PUBLICATIONS

"Composition Compensated Paper Ash Gauge", O. L. Utt and B. Y. Cho, Industry Oriented Conference and Exhibit, 1975.
"A New TiO$_2$ Compensated X-ray Ash Sensor for Paper", B. Y. Cho and O. L. Utt, 1975.
Co-pending U.S. application Ser. No. 07/310,037 for System and Process for Determining the Basis Weight of a Low Atomic Number Material in a Mixture with a Higher Atomic Number Material.
Co-pending U.S. patent application Ser. No. 07/274,645 for System and Process for Measuring Ash in Paper.

Primary Examiner—Carolyn E. Fields
Assistant Examiner—David P. Porta
Attorney, Agent, or Firm—Spensley Horn Jubas & Lubitz

[57] ABSTRACT

An x-ray sensor for determining the amount and composition of a multi-component material is disclosed. The sensor is particularly useful for determining the amount and chemical composition of a coating spread on a continuously moving paper sheet or filler material mixed into such a sheet.

15 Claims, 2 Drawing Sheets

X-RAY COATING WEIGHT CONTROLLER AND SENSOR

BACKGROUND OF THE INVENTION

The present invention relates to an apparatus and process for measuring and controlling the basis weight and composition of a coating applied to a sheet, or a filler mixed in the base sheet material, wherein the coating or filler includes at least 3 components of differing atomic weight.

For the purposes of simplicity and clarity, the following discussion relates to the use of x-ray analysis to determine the amount and composition of "ash" applied in or on a moving sheet of paper being manufactured on a papermaking machine. However, the invention is not limited to use with paper sheet, nor to an ash coating or filler material, nor to x-rays. The present invention may be used with other sheet materials, with other coating and filler materials, and with electromagnetic radiation of various energies.

Paper is generally made of three constituents: water, wood pulp fiber, and ash. "Ash" is defined as that portion of the paper which remains after complete combustion. In particular, ash may include various mineral components such as chalk (alternatively referred to as calcium carbonate or $CaCO_3$), titanium dioxide ($TiO_2$), and clay (a major component of clay is $SiO_2$).

Because certain of the components of ash may be less expensive than other components and because the relative amounts of the ash components effect the physical properties of the finished paper product, such as the opacity and brightness of the paper, it is desirable to be able to measure the amounts of the various ash components during the papermaking process. Based upon these measurements, the total amount of ash added to the sheet and the relative amounts of the individual ash components are preferably controlled to optimize the desired paper characteristics and minimize cost.

Ash may include various other non-combustible materials in addition to or in place of calcium carbonate, titanium dioxide, and clay, such as, for example, iron oxide (FeO). Iron oxide is used to make reddish-brown colored paper. However, many paper manufacturers use clay, titanium dioxide and calcium carbonate for typical white paper sheet. Furthermore, clay is generally far cheaper than wood pulp fiber. Therefore, it is often important to maintain the clay content as high as reasonably possible, while still maintaining other physical characteristics of the paper within the desired specification limits.

The total amount of ash in paper and the composition of the ash can be controlled manually by setting the rates of flow of clay and other ash components as well as the flow of wood pulp fiber and water to the papermaking system. The resulting sheet is periodically sampled and burned in the laboratory to determine the composition and amount of ash in the sheet. When the ash content is determined in the laboratory, the paper is burned under predetermined conditions and the resulting ash is accurately weighed and chemically analyzed. The papermaking parameters can then be altered based upon the resulting measurements. However, this procedure of manual control suffers from the main disadvantage that it is time consuming. Thus, large quantities of paper which do not meet specifications may be manufactured while the laboratory tests are being conducted.

The relatively long time needed for laboratory ash measurements can be particularly troublesome when the ash is contained in a coating applied to the surface of the paper sheet, rather than being mixed into the sheet itself. In the former situation, a device known as a "coater" is used to apply the ash-containing coating material to one or both surfaces of the sheet. Because the coating material will usually be applied as an extremely thin layer, coaters require essentially continuous automatic monitoring and adjustment at numerous positions (called "slices") across the width of the sheet to maintain the coating within specification limits. Therefore, when manufacturing a coated sheet, a papermaker usually cannot afford to wait for laboratory ash measurements without running the risk of producing substantial amounts of coated paper which is outside specification limits, and therefore potentially unusable.

The prior art discloses a method of using x-ray analysis during the papermaking process to determine the total amount of ash or amounts of the individual ash components mixed into a moving sheet of paper. This is accomplished by directing one or more x-ray beams into the paper and detecting that portion of the beam or beams which is transmitted through the sheet.

The proportion of an x-ray beam which is transmitted though the sheet is called its transmittance, T, and is equal to the ratio of the beam intensity before and after the beam is transmitted through the sheet, that is:

$$T = I/I_o. \tag{1}$$

Where:

I = intensity of the beam after it is transmitted through the sheet; and

Io = intensity of the beam before it is transmitted through the sheet.

The transmittance of the beam through the sheet is defined by Beer's law, as follows:

$$T = e^{-u_T W_T}. \tag{2}$$

Where:

$u_T$ = effective mass absorption coefficient of all the different constituent materials forming the sheet; and $W_T$ = total mass of these constituent materials.

Typically, when sheet materials are being measured, $W_T$ = is expressed as a "basis weight", that is, in units of mass per unit surface area of the sheet.

For sheet materials which include several constituents, such as a paper sheet including an ash-containing filler or coating, the exponent of equation (2) can be expanded, thus:

$$u_T W_T = u_{ash} W_{ash} + u_{fiber} W_{fiber} + u_{water} W_{water}. \tag{3}$$

Where:

$u_{ash}$ = mass absorption coefficient of the ash;

$W_{ash}$ = basis weight of the ash;

$u_{fiber}$ = mass absorption coefficient of the fiber;

$W_{fiber}$ = basis weight of the fiber;

$u_{water}$ = mass absorption coefficient of the water; and $W_{water}$ = basis weight of water.

The mass absorption coefficients for fiber and water are known. Further, paper making machines typically include sensors to determine both the water or moisture content and the basis weight of the paper sheet. Therefore, $W_{water}$ and $W_T$ are also known. The weight of the fiber can be expressed in terms of the basis weight of the sheet minus the weight of the ash and water in the sheet, as follows:

$$W_{fiber} = W_T - (W_{ash} + W_{water}) \quad (4)$$

Therefore, only the ash term of equation (3), i.e., $u_{ash} \cdot W_{ash}$, is unknown.

For multi-component ash materials including clay, calcium carbonate and titanium dioxide, the ash term of equation 3 can be still further expanded, thus:

$$u_{ash}W_{ash} = u_{clay}W_{clay} + u_{Ca}W_{Ca} + u_{Ti}W_{Ti} \quad (5)$$

Where:

$u_{clay}$ = mass absorption coefficient of clay;
$W_{clay}$ = basis weight of clay;
$u_{Ca}$ = mass absorption coefficient of $CaCO_3$;
$W_{Ca}$ = basis weight of $CaCO_3$;
$u_{Ti}$ = mass absorption coefficient of $TiO_2$; and
$W_{Ti}$ = basis weight of $TiO_2$.

The mass absorption coefficients, $u_{clay}$, $u_{Ca}$, and $u_{Ti}$, are known functions of the x-ray beam tube target voltage, the spectral width of the x-ray beam, and the spectral configuration of the x-ray beam, i.e., the magnitudes of the various energies contained within the x-ray beam spectrum. As a result, the only remaining unknowns in equation (5) are $W_{clay}$, $W_{Ca}$, and $W_{Ti}$, that is, the basis weight of each of the individual ash components.

By measuring the transmittance through the ash-containing sheet of 3 x-ray beams having different and independent spectral configurations, it is possible to establish 3 independent equations, one for each beam in the form of equation (2) where, for beams 1, 2 and 3:

Beam 1: $u_{ash1}W_{ash} = u_{clay1}W_{clay} + u_{Ca1}W_{Ca} + u_{Ti1}W_{Ti}$ (6)
Beam 2: $u_{ash2}W_{ash} = u_{clay2}W_{clay} + u_{Ca2}W_{Ca} + u_{Ti2}W_{Ti}$ (7)
Beam 3: $u_{ash3}W_{ash} = u_{clay3}W_{clay} + u_{Ca3}W_{Ca} + u_{Ti3}W_{Ti}$ (8)

The simultaneous solution of these 3 equations yields the amounts of the 3 unknown ash components, $W_{clay}$, $W_{Ca}$ and $W_{Ti}$. The total amount of ash can then be determined by summing the basis weights of each of the individual ash components.

To avoid the necessity of providing 3 x-ray tubes and 3 x-ray detectors, the prior art has suggested the use of a single high voltage x-ray tube whose anode voltage is successively incremented to three different voltages, such that the x-ray tube is operated at 1 of 3 different voltages during each scan across the sheet. The x-ray detector signal can then be time-wise demultiplexed to correspond to the 3 different voltages.

The detector and x-ray tube are positioned on directly opposite sides of the sheet and scanned in unison back and forth across the moving sheet so that the sensor is exposed to all portions of the sheet. The directions perpendicular to the direction of motion of the sheet are called the "cross-directions." During each of the 3 scans, the detector signal is integrated. Then, following the 3 scans, the previously mentioned simultaneous equations can be solved to determine the individual amounts of each of the ash components. The individual amounts are then summed to get a value indicative of the total amount of ash.

In many situations, the ash components may be held together in the coating material by a binder, such as latex. Typically, the binder will be mixed with the ash components in some known, fixed proportion. Accordingly, by determining the total amount of ash, one can also indirectly determine the total amount of coating material applied to the sheet.

Unfortunately, however, because of the inherently slow nature of switching a high voltage power supply between different voltage outputs, such a system may practically provide, at best, basis weight and chemical composition measurements only once after every three scans. Thus, such a system will be useless in many situations where it is necessary to achieve rapid, substantially continuous cross-directional control of coating thickness at a plurality of slice positions.

The prior art also discloses the use of a single x-ray tube, wherein the energy of the x-ray beam emanating from the tube is so distributed that the effective absorption coefficients for each of the ash components is effectively equalized. Therefore, the output from such a sensor is directly indicative of the total basis weight of the ash independent of the relative proportions of the various ash components. However, because such a sensor cannot distinguish between each of the 3 ash components, the sensor, of course, cannot provide outputs indicative of the chemical composition of the ash.

SUMMARY OF THE INVENTION

According to the present invention, there are provided combinations of method steps, devices and circuitry adapted for determining the composition and total amount of a constituent of a moving sheet, which constituent may either be applied to the surface of the sheet or mixed into the base sheet material. The constituent may contain at least 3 components having different atomic weights. In the method, 3 beams of x-rays having substantially different energy distributions are directed through the sheet. The x-rays transmitted through the sheet are then detected, and first, second and third detector signals are produced in response to the 3 x-ray beams. Such signals are indicative of the intensities of the detected x-ray beams.

According to the invention, the first detector signal is calibrated to be indicative of the total amount of the 3 component ash constituent. The second and third signals are not calibrated to be indicative of the total amount of the ash constituent. Instead, the second and third x-ray beams are such that the resulting second and third signals respond in different and independent ways to the 3 components of the ash material. The 3 signals are then transmitted to a computer which utilizes the signals in the determination of the total amount of the ash material and the composition of the ash material.

The individual basis weights of each of the ash components are determined by the solution of 3 simultaneous equations in the form of equation (2), as discussed above. The computer can then rapidly and iteratively determine the total amount of ash from the first signal. Such total ash basis weight, $W_{ash}$, is simply determined by solving an equation in the form of equation (2) for $W_{ash}$. Only a single equation is needed since, from the prior solution of the 3 simultaneous equations, the relative proportions of $W_{clay}$, $W_{Ca}$ and $W_{Ti}$ are known.

One of the many advantages of the above-described sensor is that the basis weight of the total ash can be determined rapidly and essentially continuously from the first signal. Thus, this first signal can be used in the control of process parameters which require essentially continuous monitoring and adjustment. In particular, if the sensor is used on a scanner so that it is scanned back and forth across the width of the sheet, this first signal can be used to control cross-directionally variable parameters, such as coating weight at a plurality of cross-directional slice positions.

The determination of the individual basis weights of each of the ash components is produced somewhat more slowly, since it is necessary to solve the 3 simultaneous equations. However, in typical situations, the composition of the ash component will also vary slowly. Accordingly, measurement and adjustment of such composition need be made less rapidly. Thus, the present sensor is uniquely suited to many typical manufacturing situations wherein the total amount of a material applied to or mixed in with a base sheet must be rapidly monitored and controlled, but wherein the composition of such material tends to change only slowly. A particular advantage of the present invention is that both the rapidly varying basis weight and more slowly varying composition can be monitored and controlled through the use of a single sensor.

DETAILED DESCRIPTION OF THE ILLUSTRATED EMBODIMENTS

Figure 1:
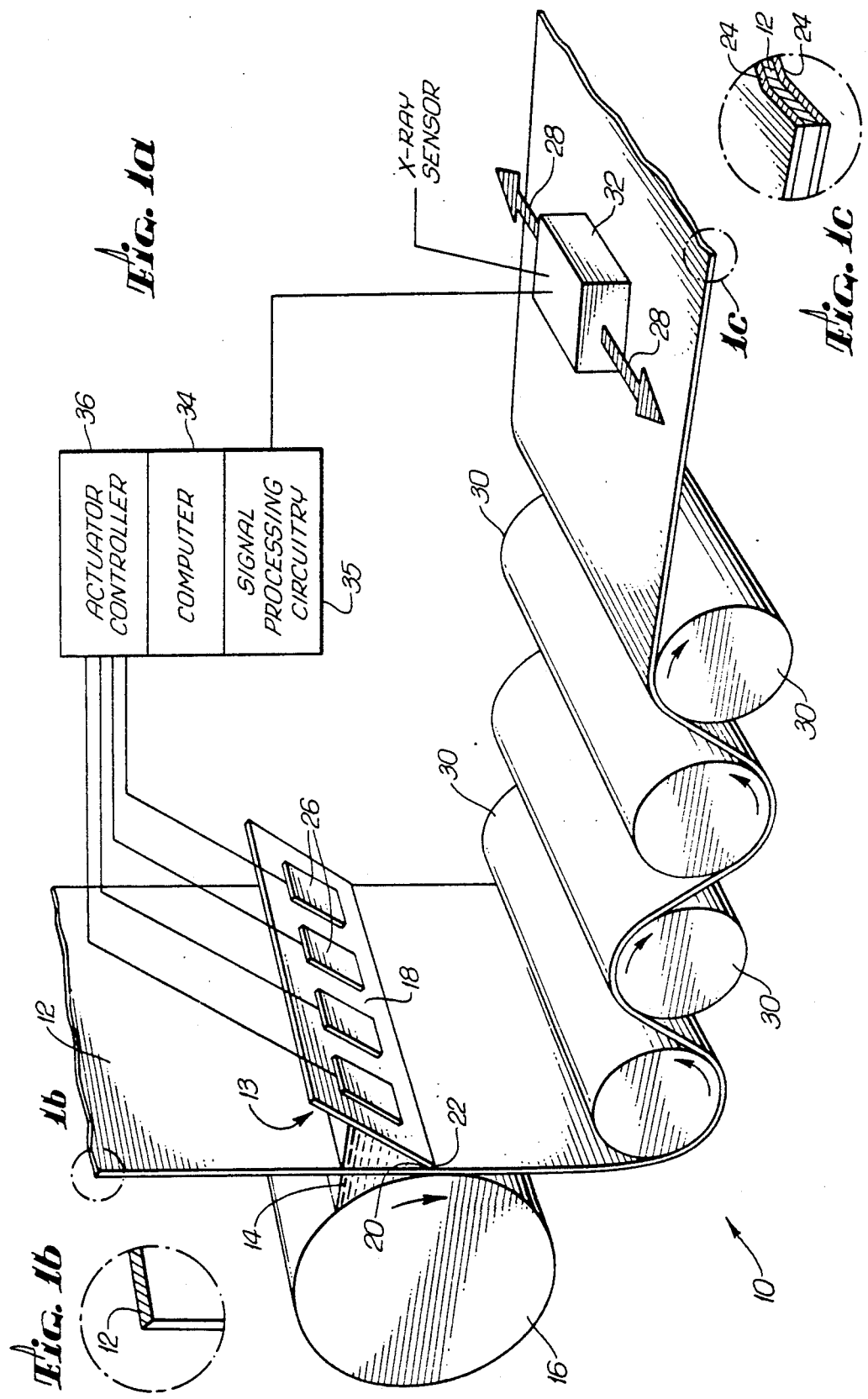
FIG. 1a is a simplified perspective schematic illustration of a sheet coating apparatus under the control of a computer and the associated x-ray sensor of the present invention.
FIG. 1b is a cross-sectional view of a portion of an uncoated paper sheet immediately prior to being coated with an ash-containing coating mixture.
FIG. 1c is a cross-sectional perspective view of a portion of the coated sheet.

The following description is of the best presently contemplated modes of carrying out the invention. This description is made for the purpose of illustrating the general principles of the invention and should not be taken in a limiting sense. The scope of the invention is best determined by reference to the appended claims.

FIG. 1a illustrates, although in highly simplified form, a paper sheet coating system 10. As illustrated in this figure, an uncoated sheet of paper 12 is drawn through a reservoir 13 of coating material 14 contained between a backing roll 16 and a blade 18. An exit slot 20 for the sheet 12 is formed between the roll 16 and the adjacent edge of the blade 18, so that the thickness of the coating on the paper 12 immediately after it exits the slot 20 is determined by the distance and pressure between the blade edge 22 and the roll 16.

Actuators 26 (for example, known pneumatic or bi-metallic electro-thermal actuators) are mounted on the blade 18 at fixed intervals and control the flexion of the blade 18 in the vicinity of each actuator 26 such that, as the actuators 26 move the blade 18 toward and away from the roll 16, the coating material on the sheet is made progressively thinner and thicker, respectively. The actuators 26 are preferably spaced at 3 or 6 inch intervals along the blade 18. Each such 3 or 6 inch interval surrounding each of the actuators is called a "slice".

After the sheet 12 exits the coating thickness control slot 20, the coated sheet passes over a number of heated drying drums 30 which dry the coating 24. The dried coated sheet then passes by the x-ray sensor 32. This sensor 32 is described in greater detail below with reference to FIG. 2.

The sensor 32 is driven back and forth across the width or cross-direction of the sheet 12 in the direction of the arrows 28, in a scanning motion so that it is able to measure the x-ray transmission through the sheet 12 at various slice positions across the width and length of the moving sheet 12.

Simplified FIG. 1 shows the sensor 32 schematically disposed only on one side of the sheet 12. In actuality, however, such a transmission sensor 32 has an x-ray source section disposed on one side of the sheet 12 and an x-ray detector section disposed on the opposite side of the sheet 12. Mechanisms (not shown) are known in the papermaking field for scanning the source and detector sections in juxtaposed relationship back and forth across the cross-direction of the sheet 12.

Signals from the scanning sensor 32 are then transmitted, via signal processing circuitry 35, to the system process control computer 34 where, as also described in greater detail below, portions of the signals are time-wise demultiplexed such that these sensor signals can be related to particular slice positions across the width of the sheet 12. The computer 34 performs various computations based upon both the continuous and demultiplexed signals to determine the basis weight of the coating 24 at each slice and the coating composition. The computer 34 compares the measured coating basis weight for each slice to a predetermined desired value and instructs the actuator controller 36 to develop control signals which cause the actuators 26 to flex the blade 18 at each slice position, as needed, to provide a desired coating basis weight for each slice. Usually, a uniform coating basis weight will be the desired goal.

Figure 2:
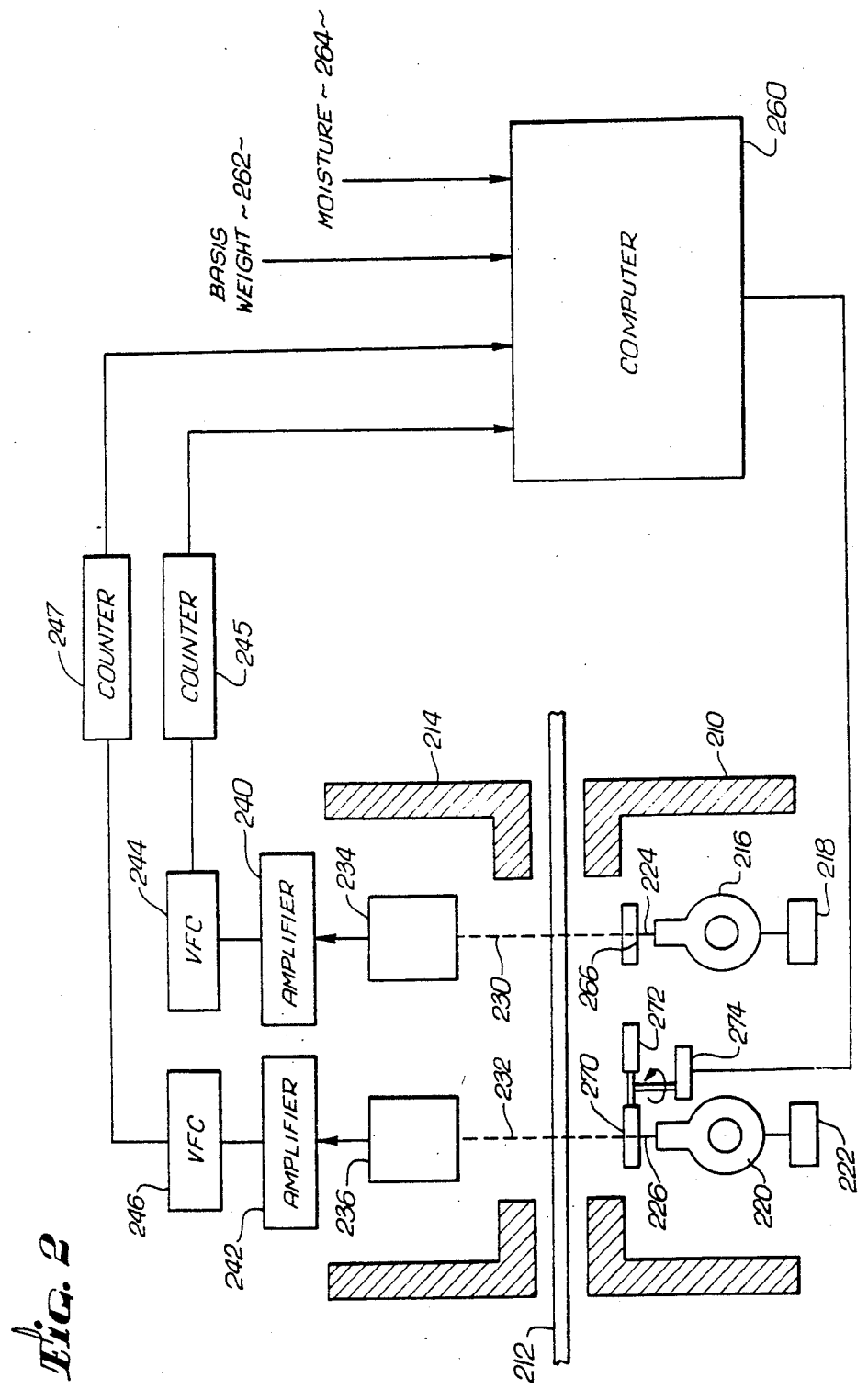
FIG. 2 is a more detailed schematic illustration of the x-ray sensor portion of the present invention and associated circuitry.

With reference to FIG. 2, one embodiment of the x-ray sensor of the present invention includes a source housing 210 located to one side of a moving sheet of paper 212. A detector housing 214 is located on the side of the paper 212 directly opposite the source housing 210, and both housings 210 and 214 are constructed and arranged to be movable in synchronized fashion across the sheet of paper 212 so that various measurements of ash can be made at each cross-directional slice position across the width of the sheet 212. As previously mentioned, various types of scanning systems (not shown) are available to move the housings 210 and 214 synchronously and in constantly opposed relationship.

The source housing 210 contains two x-ray sources, the first source includes an x-ray tube 216 coupled to a power supply 218 and a second x-ray tube 220 coupled to a second power supply 222. The first and second x-ray tubes 216 and 220 generate first and second x-ray beams 224 and 226, respectively. The portion of the first x-ray beam 224 which passes through the sheet 212 is designated as beam 230, and the portion of the second x-ray beam 226 which passes through the sheet 212 is designated as beam 232.

The detector housing 214 contains a first x-ray detector 234 which is mounted to receive the beam 230, and a second x-ray detector 236 mounted to receive the beam 232. In practice, the detectors 234 and 236 can be krypton-filled ion chambers with beryllium windows. Beryllium is highly transparent to x-rays so that the x-rays received by the detectors generate currents in the ion chambers. These currents are proportional to the strength of the x-ray beams entering the chambers.

The two detectors 234 and 236 are electrically coupled to amplifiers 240 and 242 which generate analog electrical signals having amplitudes proportional to the currents from the detectors 234, 236. The outputs of these amplifiers, 240 and 242, are electrically coupled to voltage-to-frequency converters 244 and 246 which, in turn, convert the DC analog signals from the amplifiers, 240, 242, into alternating signals having frequencies dependent upon the magnitude of the amplifier outputs. The AC signals from these voltage-to-frequency converters 244 and 246 are then fed to frequency counters 245 and 247, respectively. These counters convert the analog AC signals into digital signals and transmit the same to the computer 260.

The computer also receives signals, shown at 262 and 264, indicative of the basis weight of the coated sheet and the moisture content of such sheet. Such basis weight and moisture signals can be generated by any one of a variety of well known basis weight and moisture sensors (not shown).

In the illustrated embodiment, the sheet coating 24 includes clay, titanium dioxide and calcium carbonate held together with a latex binder, and the energy of the first x-ray beam, 224, after passing through the filter 266, is so distributed that the average effective x-ray absorption coefficients for clay, chalk and titanium dioxide are substantially equalized. To achieve this result, the x-ray source unit contains an x-ray tube 216 energized by the voltage supply 218 at approximately 6.559 kilovolts. The resulting bremstralung x-rays are then passed through the filter. The filter 266 is designed and selected to selectively absorb x-rays having energies between the K-edge energies for calcium and titanium. This particular selectivity may be achieved, for example, with a 0.1165 mil tin film filter 266. The filter 266 may be positioned as shown in FIG. 2, immediately before the x-ray beam leaves the x-ray source half of the sensor. Alternatively, the tin may be applied, for example, by vapor deposition as a coating to the beryllium window of the x-ray detector. The thickness of the tin filter will depend upon the amount of x-rays produced by the x-ray tube and the sensitivity of the detectors. Typically, however, the tin will have a thickness of about 0.1 mil.

The signal provided by the detector 234 is amplified and digitized, as described above. The digitized signal is then transmitted to the computer 260 which utilizes the signal in the production of an on-line response indicative of the total amount of the ash in the coating layer then being penetrated by x-ray beam 230. The response may be displayed, for example, on a CRT or other recording device and also utilized the automatic control of the coating blade 18, for example, in the manner described above in connection with FIG. 1.

The second x-ray tube/detector pair, 220 and 236, includes 2 x-ray filters, 270 and 272, which may be alternately inserted into the path of the x-ray beam 226. As illustrated in FIG. 2, the 2 filters, 270, 272, are mounted in a rotating wheel. The wheel may be rotated to periodically dispose either filter 270, 272 in the path of the x-ray beam 226. The movement of such filters 270, 272 into and out of the x-ray beam 226 is effectuated by a motor 274 operated under control of the computer 260. Accordingly, by alternately inserting the 2 filters 270, 272 into the beam 226, the energy distribution of the second x-ray beam 232 may be first tuned for equal sensitivity to calcium carbonate and titanium dioxide, but different sensitivity to clay with filter 270. Then, by switching filters so that filter 272 is in the path of the x-ray beam 226, the beam is subsequently tuned for equal sensitivity to titanium dioxide and clay, but different sensitivity to calcium carbonate. To achieve these tunings, filter 270 may be made of a 1.000 mil thick aluminum foil and filter 272 made from two stacked thin films, wherein one is made of 1.000 mil thick aluminum and the other is made of 0.345 mil thick titanium. Alternatively, because the aluminum film has the same thickness in both filters, 270 and 272, the aluminum filter may be fixedly mounted in the path of the beam 226 or deposited on the beryllium window of detector 236. In this case, only the titanium filter need be rotated into and out of the path of the beam 226.

The signals from the second x-ray detector 236 are then time-wise demultiplexed in accordance with which filter 270, 272 is disposed in the path of the x-ray beam 226. In effect, the second x-ray tube/detector pair 220, 236 serves the function of 2 separate x-ray tubes and two separate corresponding x-ray detectors, depending upon which of the 2 filters is disposed in the path of the x-ray beam.

The signal from the first detector 234 plus the time-wise demultiplexed signals from the second detector 234 may be combined in 3 simultaneous equations, as discussed in greater detail below, to determine the individual basis weights of the 3 ash components of the coating material. In addition, as previously mentioned, the signal from the first x-ray detector 234 may be utilized singly by the computer 260 to provide a substantially continuous reading of the total basis weight of the ash-containing sheet coating.

In the present preferred embodiment, the filter 266 is chosen such that $u_{clay} = u_{Ca} = u_{Ti}$ for the first signal originating with the detector 234. By appropriate choice of x-ray filters, the 2 demultiplexed signals from the second x-ray detector 236 (1 signal being associated with each of the 2 alternating filters 270, 272) may be chosen such that $u_{Ca} = u_{Ti}$ when filter 270 is in the path of the x-ray beam 226 and $u_{clay} = u_{Ti}$ when filter 272 is in the path of the x-ray beam 226. Accordingly, in the case of the detector signal from detector 234 where the absorption coefficients for each of the 3 ash components of the coating material are equalized, substituting these absorption coefficient values into equations (2), (3) and (5) and simplifying yields:

$$W_{ash} = \frac{-1}{u_{ash}} \ln(T). \tag{9}$$

Where $u_{ash} = u_{clay} = u_{Ca} = u_{Ti}$, and x-ray absorption by the fiber and water are assumed to be negligible. This is typically an accurate assumption. If, however, x-ray absorption by the fiber and water is not negligible, then the computed value for $W_{ash}$ can be corrected for such absorption since, as previously mentioned, the absorption coefficients of water and fiber are known, and their basis weights can be determined.

In this manner, the single x-ray signal from the first detector 234 can be used to calculate the total amount of ash, and hence the total amount of coating 24 applied to the paper sheet 12. Simultaneous solution of 3 such equations, one for each of the 3 signals (i.e., the signal from detector 234 and the 2 time-wise demultiplexed signals from detector 236), yields the individual ash components.

In a second presently preferred embodiment, an isotopic x-ray source, such as Fe-55 is substituted for the x-ray tube 216 and associated power supply 216. Fe-55 yields a monochromatic x-ray beam having an energy of approximately 7 kilo-electron volts.

The use of an isotopic x-ray source has several advantages over the use of an x-ray tube. For example, an Fe-55 source naturally produces x-rays at an invariant monochromatic energy. Accordingly, the x-ray sensor can be greatly simplified, since all of the electronics needed to produce and stabilize the output of an x-ray tube become unnecessary. Therefore, the use of an isotopic x-ray source can result in a more reliable sensor. However, because Fe-55 produces a fixed monochromatic x-ray beam, unlike the broad spectrum x-ray beam generated by an x-ray tube, such a monochromatic beam cannot be filtered to substantially equalize its sensitivity to the 3 components of the ash-containing coating. Instead, when Fe-55 is used, equation (9) becomes somewhat more complicated, since no longer is $u_{ash} = u_{clay} = u_{Ti} = u_{Ca}$. Instead, $u_{clay}$, $u_{Ti}$ and $u_{Ca}$ all have different values at the single x-ray energy.

Despite the fact that the absorption coefficients for each of the 3 components are not equalized in this second embodiment, the output of detector 234 can nevertheless still be utilized to provide a substantially continuous reading indicative of the total ash basis weight. This is because $u_{clay}$, $u_{Ti}$ and $u_{Ca}$ at 7 kilovolts can be determined by prior experimentation. Therefore, in the prior equations, only the relative amounts of clay, titanium dioxide and calcium carbonate are unknown. However, by constructing 3 simultaneous equations in the form previously discussed, the first signal associated with the output from the first x-ray detector, 234, and the second and third signals associated with the timewise demultiplexed signals from the second detector 236 can be utilized in the solution of such equations to determine the relative basis weights of the clay, titanium dioxide and calcium carbonate components of the coating material. Once the relative proportions of clay, titanium dioxide and calcium carbonate in the coating mixture are known, then $u_{ash}$ can be easily computed.

In operation of the above-described second preferred embodiment using an isotopic source, the relative proportions of clay, titanium dioxide and calcium carbonate in the coating mixture are assumed to remain constant during each scan of the sensor 32 across the width of the sheet 12. This is frequently an accurate assumption. As illustrated in FIG. 1 and discussed above, the coater provides only a very thin coating 24 to the opposing surfaces of the sheet 12. Therefore, the coating material 14 in the reservoir 13 between the coater blade 18 and backing drum 16 needs to be supplemented only relatively infrequently. Thus, the composition of the coating mixture 14 should remain substantially constant over relatively long periods of time.

Since the relative percentages of clay, titanium dioxide and calcium carbonate in the coating mixture remains substantially constant during the period of time necessary to complete a scan across the sheet 12, the output signal from the first detector 236 can be utilized to provide a substantially continuous and immediate reading indicative of the total basis weight of the coating at each slice as the sensor 32 is scanned across the sheet 12. At the end of each scan, however, the computer 260 can combine the time-wise demultiplexed signals from the second x-ray tube/detector pair, 220, 236, and, utilizing the 3 simultaneous equations discussed above, recompute the relative basis weights of the clay, titanium dioxide and calcium carbonate components. During the next scan, the value of $u_{ash}$ is updated according to the most recently calculated coating mixture composition and, during this subsequent scan, the updated value of $u_{ash}$ is used to again provide a substantially continuous output indicative of the coating basis weight at each slice.

As previously discussed, the chemical composition of the coating mixture 14 remains substantially constant during the period of time necessary to complete a single scan across the sheet 12. However, at the end of each scan, the computer 260 utilizes the 3 simultaneous equations to recompute the composition of the coating mixture 14. At the end of each scan, this recomputed coating mixture composition may then be utilized to adjust the relative amounts of clay, titanium dioxide and calcium carbonate fed to the mixing tank (not shown) used to supply the reservoir 13 with the coating mixture 14. Thus, with an x-ray sensor constructed according to the present invention, a substantially continuous reading of the coating basis weight can be obtained to substantially continuously control the coater blade 18. Simultaneously, and without the need for a totally separate sensor system, periodic measurements of the coating composition can be obtained and utilized to adjust the chemical composition of the coating mixture 14. Although the coating composition readings are obtained less rapidly than the substantially continuous reading of total coating basis weight, the relatively small delay in periodically updating the coating composition reading has no adverse effect on coating composition control since, as previously discussed, the coating composition changes relatively slowly when compared to the basis weight.

Although the present invention has been described and illustrated in connection with two presently preferred embodiments, this relatively detailed description is illustrative only and not restrictive. For example, the present invention may be used to measure the total basis weight and chemical composition of filler mixed into the base sheet, as well as coating material applied to the surface of such sheet. Also, the present invention is not limited to use with transmission-type x-ray sensors, reflection-type sensors may also be used. Many changes and modifications are within the spirit and scope of the invention and will be apparent t those of ordinary skill in the art based upon the present disclosure.

We claim:

1. An apparatus for measuring a 3 component first material associated with a second material, the apparatus comprising:
   source means for directing first, second and third x-ray beams through the first and second materials;
   detector means for detecting the three x-ray beams after they are transmitted through the first and second materials and for producing first, second and third signals in response to the first, second and third beams respectively;
   a computer, operatively coupled to the detector means for receiving the first, second and third signals, the computer being programmed to substantially continuously determine the amount of the first material associated with second material based upon the first signal, the substantially continuous determination being periodically adjusted based upon changes in the second and third signals.

2. The apparatus of claim 1, wherein the detector means includes first and second x-ray detectors and the source means includes a first x-ray source disposed to direct a first beam of x-rays toward the first x-ray detector and a second x-ray source disposed to alternately direct the second and third beams of x-rays toward the second detector.

3. The apparatus of claim 2, wherein the second x-ray source includes an x-ray tube disposed to direct a beam of x-rays toward the second detector, first and second x-ray filters and switching means for selectively inserting the first and second filters into the path of the x-ray beam.

4. The apparatus of claim 3, wherein the first x-ray source produces an x-ray beam having energies distributed to yield equalized effective absorption coefficients for each of the three components of the first material.

5. The apparatus of claim 3, wherein the first x-ray source is a source of monochromatic x-rays.

6. The apparatus of claim 5, wherein the first x-ray source is an isotopic x-ray source.

7. The apparatus of claim 6, wherein the isotope is Fe-55.

8. The apparatus of claim 1, further comprising means for periodically computing the amounts of the 3 components in the first material.

9. A method for measuring a 3 component first material, the method comprising the steps of:
   directing first, second and third x-ray beams through the first material;
   producing first, second and third responses indicative, respectively, of the intensity of the first, second and third x-ray beams which are transmitted through the material; and
   periodically determining, at a first rate, the amount of the first material based upon the first response and periodically adjusting the determination of the amount of the first material based upon the second and third responses, the periodicity of the adjustment occurring at a second rate which is less frequent than the first rate.

10. The method of claim 9, wherein the energy distribution of the first beam yields substantially equalized x-ray absorption coefficients for each of the three components.

11. The method of claim 9, wherein the first x-ray beam is monochromatic.

12. The method of claim 11, wherein the first x-ray beam emanates from an isotopic x-ray source.

13. The method of claim 12, wherein the isotopic x-ray source is Fe-55.

14. The method of claim 9, further comprising the steps of periodically determining the amounts of each of the three components in the first material.

15. The method of claim 14, wherein the first material is a coating applied to a second material.

* * * * *